(12) United States Patent
Chatterjee

(10) Patent No.: US 7,667,022 B2
(45) Date of Patent: Feb. 23, 2010

(54) PROMOTER FOR HIGH-THROUGHPUT SCREENING FOR INHIBITORS AGAINST MYCOBACTERIA UNDER LOW CARBON CONDITIONS

(75) Inventor: Deepankar Chatterjee, Bangalore (IN)

(73) Assignee: Council of Scientific & Industrial Research, New Delhi (IN)

( * ) Notice: Subject to any disclaimer, the term of this patent is extended or adjusted under 35 U.S.C. 154(b) by 165 days.

(21) Appl. No.: 10/764,553

(22) Filed: Jan. 27, 2004

(65) Prior Publication Data

US 2005/0095252 A1  May 5, 2005

Related U.S. Application Data

(60) Provisional application No. 60/442,511, filed on Jan. 27, 2003.

(51) Int. Cl.
*C07H 21/04* (2006.01)
*C12P 21/06* (2006.01)

(52) U.S. Cl. .................................. 536/24.1; 435/69.1

(58) Field of Classification Search .................. None
See application file for complete search history.

(56) References Cited

U.S. PATENT DOCUMENTS 4,753,876 A * 6/1988 Hemming et al. ............. 435/34
6,294,328 B1 * 9/2001 Fleischmann et al. .......... 435/6

OTHER PUBLICATIONS

Avarbock et al., Gene, 1999, vol. 233, pp. 261-269.*
Ojha et al., Infection and Immunity, 2000, vol. 68, No. 7, pp. 4084-4091.*

* cited by examiner

*Primary Examiner*—Nancy Vogel
*Assistant Examiner*—Catherine Hibbert
(74) *Attorney, Agent, or Firm*—Sughrue Mion, PLLC

(57) ABSTRACT

The present invention relates to a promoter for high-throughput screening for inhibitors against Mycobacteria under low carbon or starved conditions. Further, the use of this novel 200 bp promoter open new vistas and provides a new system that would enable the TB drug developers to isolate and develop highly efficient inhibitors or medicines against ever evolving and changing *M. tuberculosis* mycobacteria.

5 Claims, 10 Drawing Sheets

Figure 2:
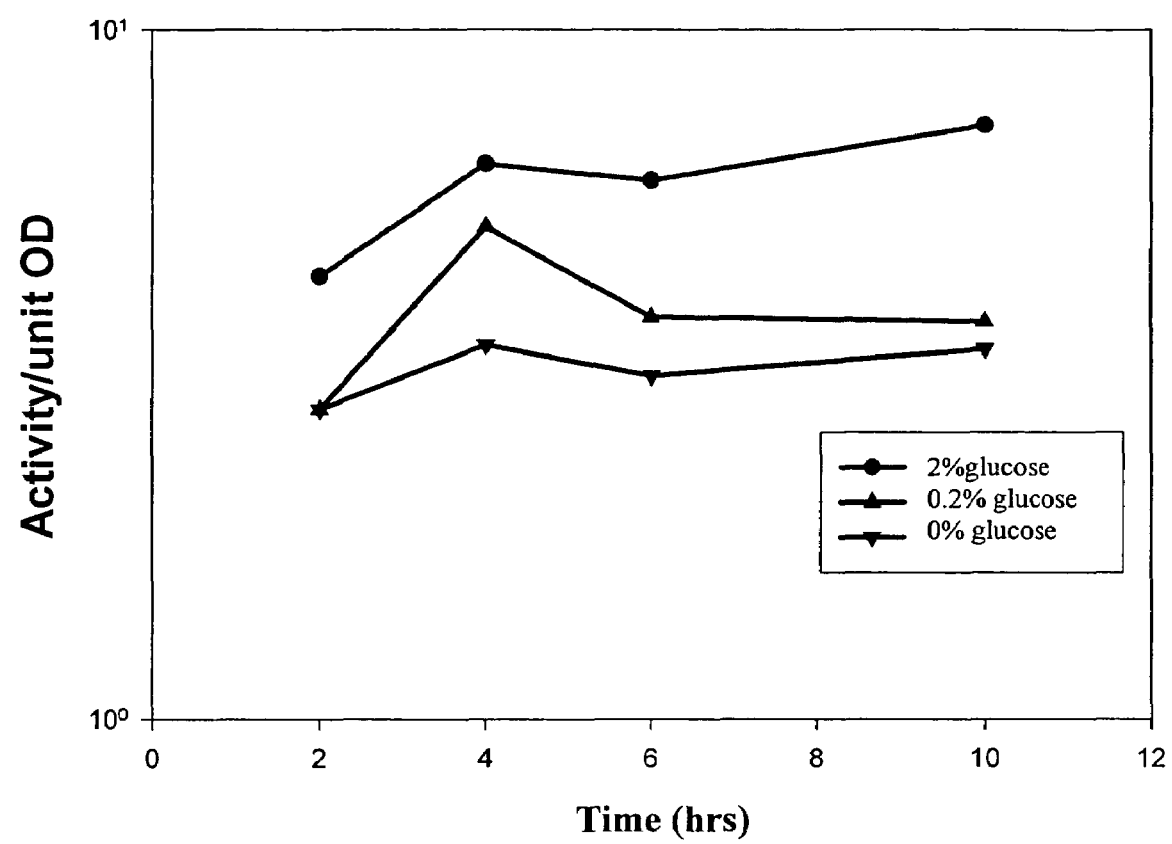

BamHI
|
GGATCCCTGGTAACCCCCGACAGCTACCAGCGCACCGACTACCCGTCGGCCGGGATCGAGCAGCTGATC

TTCGCACCACAAGGTTCACTCGCGCAAAGCCGCACCCGCCGCGCGCTCGCGTTGTGTGTACCCCGGGAC

GCGATCGCTCGGGATGCCGGGGTTCCGATTGCCAACTCGCGGCTGTCCCCGGCGACCGACGATGCCCTC

ACCGATGCCGACGGCGCCGCCGAAGCACGTCAGTTCGGCCGGGTGGACCCCGCCGCCGCTCGCGACGCG

CTGGGTGGTACGCCGCTGACCGTGCGGATCGGCTACGGCAGGCCCAACGCTCGGTTGGCGGCCACCATC

GGAACCATTGCCGACGCCTGCGCCCCGGCCGGGATCACCGTTTCGGATGTGACGGTGGACACACCCGGA

CCGCAAGCGCTGCGGGACGGAAAGATTGACGTATTGTTGGCGAGCACCGGTGGGGCCACCGGCAGCGG

ATCGAGCGGATCGTGTGCGATGGATGCCTATGACTTGCACAGCGGCAACGGAAACAATCTATCGGGGTA

CGCAAACGCTCAGATCGACGGCATCATCAGCGCGCTCGCGGTGTCGGCCGACCCCGCCGAGCGGGCCAG

GTTGCTTGCCGAGGCCGCGCCGGTGCTCTGGGATGAGATGCCAACCTTGCCGTTGTACCGGCAGCAGCG

CACGTTGTTGATGTCGACGAAAATGTATGCGGTGAGCAGGAATCCGACGCGATGGGGGGCAGGGTGGA

ACATGGATCGCTGGGCGCTGGCGCGGTGACGATGGCCAGTGCCATCTGCAGGTAATTGACAGAATTCCA

CGACGAGAAGCGGACTATCGGAGCGTAGTGTCGCAGGTGCTCCGGGCTGTCTGGGAGAGGATGTGTGCC

ATGGCGGTACATGGGCTGGTGACTACGTGTTGAACGTGATCGCGACGGGGCTCTCCTTAAAGGCACGGG

GGAAGCGCCGCCGGCAGCGTTGGGTCGACGACGGGCGGGTATTGGCGCTCGGTGAGTCCCGCCGGAGCT

CAGCCATATCTGTGGCCGACGTGGTTGCGTCGCTGACCCGGGATGTGGCCGACTTTCCGGTTCCCGGCGT

CGAGTTCAAGGACCTCACCCCGCTATTCGCCGACCGAAGAGGATTGGCCGCGGTAACCGAAGCGCTGGC

CGATCGGGCGTCCGGAGCTGACCTGGTGGCCGGCGTCGACGCCCGCGGGTTTCTGGTGGCAGCCGCGGT

CGCCACCCGGCTCGAAGTGGGTGTGCTGGCCGTTCGCAAGGGCGGCAAGCTGCCCCGGCCGGTGCTCAG

CGAGGAGTACTACAGGGCGTACGGCGCCGCCACTCTGGAGATTCTCGCTGAGGGCATCGAGGTTGCGGG

Sak2 ———▶
CCGCCGTGTCGTGATCATTGACGACGTGTTAGCAACCGGCGGCACCATCGGCGCGACGCGACGCCTGCT

TGAGCGCGGTGGCGCCAACGTGGCCGGGGCGGCCGTAGTGGTGGAACTTGCGGGGTTGAGCGGTCGCGC

GGCGCTCGCACCGCTGCCGGTGCACAGCCTGAGCCGCCTGTGAGGGATATCCTCTAGGTCGGAGGTGAC

◀——— Sak1
GAACGTGGCCGAGGACCAGCTCACGGCGCAAGCGGTTGCACCGCCCACGGAGGCTTCTGCGGCTCTCGA

GCCCGCTCTCGAGACGCCCGAGTCGCCGGTCGAGACTCTTAAGACCAGCATCAGCGCGTCGCGTCGGGT

GCGGGCCCGATTGGCCCGGCGGATGACCGCCCAGCGCAGCACCACCAATCCGGTGCTCGAGCCGTTGGT

GGCGGTGCACCGGGAGATCTATCCCAAGGCCGACCTGTCGATCTTGCAGCGAGCCTACGAGGTCGCTGA

CCAAAGGCATGC
      |
SphI  BglII
|     |

Figure.1

−10 Consensus sequence of M.tuberculosis promoter

| T | A | y | G | A | T |
|---|---|---|---|---|---|
| 80% | 90% | 60% | 40% | 60% | 100% |

−10 Consensus sequence of rel Promoter

| | T | A | T | C | C | T |
|---|---|---|---|---|---|---|
| Mutation | ↓ | | ↓ | | | ↓ |
| | G | | G | | | C |

Figure 8.

SEQUENCE LISTING

<160> NUMBER OF SEQ ID NOS: 4

<210> SEQ ID NO 1
<211> LENGTH: 1874
<212> TYPE: DNA
<213> ORGANISM: Mycobacterium tuberculosis

<400> SEQUENCE: 1
ggatccctgg taaccccga cagctaccag cgcaccgact acccgtcggc cgggatcgag    60
cagctgatct tcgcaccaca aggttcactc gcgcaaagcc gcaccgccg cgcgctcgcg   120

```
ttgtgtgtac cccgggacgc gatcgctcgg gatgccgggg ttccgattgc caactcgcgg      180
ctgtccccgg cgaccgacga tgccctcacc gatgccgacg gcgccgccga agcacgtcag      240
ttcggccggg tggaccccgc cgccgctcgc gacgcgctgg gtggtacgcc gctgaccgtg      300
cggatcggct acggcaggcc caacgctcgg ttggcggcca ccatcggaac cattgccgac      360
gcctgcgccc cggccgggat caccgtttcg gatgtgacgg tggacacacc cggaccgcaa      420
gcgctgcggg acggaaagat tgacgtattg ttggcgagca ccggtggggc caccggcagc      480
ggatcgagcg gatcgtgtgc gatggatgcc tatgacttgc acagcggcaa cggaaacaat      540
ctatcggggt acgcaaacgc tcagatcgac ggcatcatca gcgcgctcgc ggtgtcggcc      600
gaccccgccg agcgggccag gttgcttgcc gaggccgcgc cggtgctctg ggatgagatg      660
ccaaccttgc cgttgtaccg gcagcagcgc acgttgttga tgtcgacgaa aatgtatgcg      720
gtgagcagga atccgacgcg atgggggca gggtggaaca tggatcgctg gcgctggcg       780 cggtgacgat ggccagtgcc atctgcaggt aattgacaga attccacgac gagaagcgga      840
ctatcggagc gtagtgtcgc aggtgctccg ggctgtctgg gagaggatgt gtgccatggc      900
ggtacatggg ctggtgacta cgtgttgaac gtgatcgcga cggggctctc cttaaaggca      960
cgggggaagc gccgccggca gcgttgggtc gacgacgggc gggtattggc gctcggtgag     1020
tcccgccgga gctcagccat atctgtggcc gacgtggttg cgtcgctgac ccgggatgtg     1080
gccgactttc cggttcccgg cgtcgagttc aaggacctca ccccgctatt cgccgaccga     1140
agaggattgg ccgcggtaac cgaagcgctg ccgatcgggc gtccggagc tgacctggtg     1200 gccggcgtcg acgcccgcgg gtttctggtg gcagccgcgg tcgccacccg gctcgaagtg     1260
ggtgtgctgg ccgttcgcaa gggcggcaag ctgccccgc cggtgctcag cgaggagtac     1320
tacagggcgt acggcgccgc cactctggag attctcgctg agggcatcga ggttgcgggc     1380
cgccgtgtcg tgatcattga cgacgtgtta gcaaccggcg gcaccatcgg cgcgacgcga     1440
cgcctgcttg agcgcggtgg cgccaacgtg gccggggcgg ccgtagtggt ggaacttgcg     1500
gggttgagcg gtcgcgcggc gctcgcaccg ctgccggtgc acagcctgag ccgcctgtga     1560
gggatatcct ctaggtcgga ggtgacgaac gtggccgagg accagctcac ggcgcaagcg     1620
gttgcaccgc ccacggaggc ttctgcggct ctcgagcccg ctctcgagac gcccgagtcg     1680
ccggtcgaga ctcttaagac cagcatcagc gcgtcgcgtc gggtgcgggc ccgattggcc     1740
cggcggatga ccgcccagcg cagcaccacc aatccggtgc tcgagccgtt ggtggcggtg     1800
caccgggaga tctatcccaa ggccgacctg tcgatcttgc agcgagccta cgaggtcgct     1860
gaccaaaggc atgc                                                      1874
```

<210> SEQ ID NO 2
<211> LENGTH: 266
<212> TYPE: DNA
<213> ORGANISM: Mycobacterium tuberculosis

<400> SEQUENCE: 2

```
cgccgccact ctggagattc tcgctgaggg catcgaggtt gcgggccgcc gtgtcgtgat       60
cattgacgac gtgttagcaa ccggcggcac catcggcgcg acgcgacgcc tgcttgagcg      120
cggtggcgcc aacgtggccg gggcggccgt agtggtggaa cttgcggggt tgagcggtcg      180
cgcggcgctc gcaccgctgc cggtgcacag cctgagccgc ctgtgaggga tatcctctag      240
gtcggaggtg acgaacgtgg ccgagg                                            266
```

```
<210> SEQ ID NO 3
<211> LENGTH: 28
<212> TYPE: DNA
<213> ORGANISM: Artificial Sequence
<220> FEATURE:
<223> OTHER INFORMATION: PCR primer

<400> SEQUENCE: 3
cggccacgtt cggtacctcc gacctaga                                          28

<210> SEQ ID NO 4
<211> LENGTH: 30
<212> TYPE: DNA
<213> ORGANISM: Artificial Sequence
<220> FEATURE:
<223> OTHER INFORMATION: PCR primer

<400> SEQUENCE: 4
gccgtgtcgt gagaattcac gacgtgttag                                        30
```

PROMOTER FOR HIGH-THROUGHPUT SCREENING FOR INHIBITORS AGAINST MYCOBACTERIA UNDER LOW CARBON CONDITIONS

This application claims benefit of Provisional Application No. 60/442,511 filed Jan. 27, 2003; the disclosure of which is incorporated herein by reference.

FIELD OF INVENTION

The present invention relates to a promoter for high-throughput screening for inhibitors against Mycobacteria under low carbon or starved conditions, more specifically promoter sequence of rel A gene for high-throughput screening for inhibitors against Mycobacteria under low carbon or starved conditions.

BACKGROUND INFORMATION

Many bacteria can assume a well-defined physiological state under starvation, which facilitates their survival (Spector et al, 1988; Nystrome et al. 1989; Matin, A, 1991). The role of ppGpp in the developmental process of these physiological states has been a subject of interest for many researchers over the years. It has been extensively studied in *Myxococcus xanthus* where accumulation of ppGpp has been observed to be an important requirement for the formation of fruiting body (Harris et al. 1988). In *Streptomyces coelicolor*, ppGpp has been implicated in synthesis of antibiotics in the stationary phase of the bacteria (Chakraburty and Bibb, 1997). Though ppGpp has been detected in various other prokaryotes e.g. *Bacillus subtilis* (Ochi et al. 1982), *Bacillus stearothermophilus* (Fehr and Richter, 1981), *Staphylococci* (Cassesl et al. 1995), *Streptococcus equisimilis* (Mechold et al. 1996), *Salmonella typhimurium* (Kramer et al. 1988; Shand et al. 1989) under starvation, its function in these organisms is yet to be determined.

Bacteria adapt to nutritional stress for their survival predominantly through a mechanism termed the stringent response. The hallmarks of the stringent response are the accumulation of ppGpp, also called stringent factor, and down regulation of stable RNA (rRNA and tRNA) synthesis (Cashel et al. 1996). It appears that RNA polymerase is the ultimate target of ppGpp (Chatterji et al. 1998), although the exact mode of selective down regulation of the gene expression is not clear.

*Mycobacterium Smegmatis* grown under carbon depletion conditions serves as a best model of *Mycobacterium Tuberculosis* under latent conditions for drug screening.

*Mycobacterium smegmatis* is a fast growing counterpart of *M. tuberculosis* (*M. tb*), which is non-pathogenic in nature and thus easy to handle. Moreover, both these organism along with other mycobacteria share many of the characteristic features which make them suitable models for each other.

Such common metabolic pathways leading to the survival of the organism have been known sometime now. Extensive work to prove that latent *M. tb* can indeed be represented by *M. smegmatis* under depleted carbon source has been carried out and well known (Ojha et al., 2002). The studies by Ojha et al (2002) describe some recent observations to validate this model and establish that without these recent observations the present invention and model cannot be supported.

Although *Mycobacterium smegmatis* is non-pathogenic, it shares many biosynthetic pathways of *Mycobacterium tuberculosis* and may serve as a good model system. In addition, its faster growth rate makes it a suitable candidate for starvation studies. It has been shown that ppGpp accumulation is accompanied by morphological change in *M. smegmatis* under carbon starvation. Furthermore, *M. smegmatis* assumes the coccoid morphology (similar to the persistors) when ppGpp is ectopically produced by overexpression of *E. coli* relA in an enriched nutritional medium. It has also been characterized by the in vivo function of *M. tuberculosis* relA/ spoT homologue in *M. smegmatis* (Ojha et al, 2000).

The development of molecular genetic tools is needed to understand the mechanisms relating to gene expression in mycobacterial species. The slow growth rate of mycobacterial pathogens could be attributed to sluggish transcription initiation which in turn, perhaps, is due to the lower occurrence of strong promoters in a mycobacterial genome. This is one of the reasons why a sufficiently strong and inducible expression system has not yet been established for mycobacteria. This can be achieved by providing a strong mycobacterial promoter upstream from the desired gene. With such a vector, the gene of interest, from a slow growing pathogen, can be successfully expressed in the heterologous faster growing mycobacterial species, which can act as a surrogate host.

Studies on the regulation of gene expression in any system are facilitated by simple and reliable assays, which can be quantitated and monitored both in vitro or in vivo. Reporter technology thus relies on fusing an assayable expression in both homologus and heterologous systems, whose products are stable, with a promoter having a sequence that can be regulated by different signals. Reporter genes have become convenient tools for studying mycobacteria and several such systems are known in the literature (Tyagi et al., 1997). Out of the many, few have become very popular and are widely used because of their control and inducibility (Stover et al., 1991; Parish et al., 1997). Recently xylE reporter assay has been proposed for high through-put screening in mycobacteria (Dastur and Varshney, 2001) and perhaps several such systems will be necessary in order to quantitate the relative strength of each assay against a target gene in mycobacteria.

By far the best candidate for reporter assay in *E. coli* has been the lacZ expression system where the *E. coli* lacZ gene encoding β-galactosidase (Fowler and Zabin, 1983) has been extensively used with various substrates like lactose or its derivatives to catalyze the cleavage of β-1,4 linkage producing galactose and glucose as products. One of the common derivatives of lactose has been ONPG (o-nitrophenyl-β-D-galactopyranoside), which yields a colored product and can be monitored spectrophotometrically (Miller, 1972). In addition, the presence of the chromogenic substrate X-gal (5-bromo-4-chloro-3-indolyl-D-galactopyranoside) in nutrient agar plates results in blue color in colonies expressing lacZ and thus the appearance of blue or white colonies mark the presence of lacZ in solid media as opposed to ONPG assay in an aqueous environment (Timm et al., 1994a, 1994b; Bannantine et al., 1997; Jain et al., 1997). Varying degree of "blueness" in a colony, in principle can tell the relative strength of a promoter.

Several attempts have been made in the past to fuse a mycobacterial promoter sequence with lacZ with varying degrees of success (Dellagostin et al., 1995; Knipfer et al., 1998; Kumar et al., 1998). One of the problems was the instability of lacZ in *M. smegmatis* due to transposition of an element IS 1096 and subsequent deletion of the vector (Cirillo et al., 1991; Chawla and Das Gupta, 1999).

Investigations by the inventors have shown a carbon starvation induced stringent response pathway in *M. smegmatis* (Ojha et al., 2000, Chatterji and Ojha, 2001, Ojha et al., 2002). The product of stringent response (p)ppGpp is maintained within the cell by two enzymes RelA and SpoT and in gram positive organisms like mycobacteria both the enzymes are part of a same gene known as rel (Ojha et al., 2000). An earlier work of the inventors revealed the cloning and expression of 1.5 kb upstream fragment of rel from *M. tuberculosis* (Ojha et al., 2000). This gene expresses well and shows all its characteristics in the surrogate host *M. smegmatis*. In this present invention the inventors have identified a 200 base pair sequence upstream from the rel gene which when fused with lacZ shows stronger promoter activity than hsp60 promoter. This shows the identification of a −10 promoter sequence by base specific mutation and it can be observed that the plasmid bearing lacZ fused with 200 base pair rel fragment is stable.

This promoter sequence of 200 bp of the present invention is useful for high-throughput screening and developing novel inhibitors against Mycobacteria under low carbon or starved conditions. In other words, use of this novel 200 bp promoter open new vistas and provides a new system that would enable the TB drug developers to isolate and develop highly efficient inhibitors or medicines against ever evolving and changing *M. tuberculosis* mycobacteria.

OBJECTS OF THE INVENTION

The main object of the invention relates to a promoter for high-throughput screening for inhibitors against Mycobacteria under low carbon or starved conditions.

Yet another object of the present invention relates to a method of isolating a promoter for high-throughput screening for inhibitors against Mycobacteria under low carbon or starved conditions.

Still another object of the invention relates to use of a promoter for high-throughput screening and developing inhibitors against Mycobacteria under low carbon or starved conditions.

One more object of the invention relates to prevention of mycobacteria survival due to activation of the promoter under low carbon or starved conditions by identifying efficient inhibitors.

BRIEF DESCRIPTION OF ACCOMPANYING DRAWINGS/FIGURES

FIG. 1. The nucleotide sequence of 1.5 kb DNA fragment upstream of *M. tuberculosis* relA/spot (SEQ ID NO:1).

FIG. 2. Constitutive activity of 1.5 kb DNA fragment when assayed using XylE reporter system.

FIG. 3*a*. The promoter activity of 200 bp fragment immediately upstream to the start codon of *M. tuberculosis* relA/spoT. A) pSD5B (promoterless lacZ) B) pAN12(200 bp rel promoter+lacZ).

FIG. 3*b*. β-galactosidase assay showing a constitutive activity of $P_{relMt}$. Cells harboring pAN12 were grown in carbon enriched medium (2% glucose) till $OD_{600}$ of 0.7 and then transferred to 7H9 medium without any carbon source. Cells were taken out at different time intervals and their β-galactosidase activity was measured. The background activity of empty vector (pSD5B) was used as a reference.

FIG. 4. lacZ expression by 200 bp promoter region occurs in *M. smegmatis*, but not in *E. coli*. A) pAN12 transformed into *E. coli* B) pAN12 transformed into *M. smegmatis*

FIG. 5*a*. Comparative analysis of the promoter strength of PrelMt and the $P_{hsp60}$ on 7H9 agar containing X-gal, A) pSD5B (empty vector), B) pAN12, C) pMV261 (empty vector) D) pHspLac(pMV261+lacZ) transformed *M. smegmatis*.

FIG. 5*b*. PrelMt. (in pAN12) is approximately 2.5 fold stronger than Phsp60 (in pHasplac). Both the promoters were cloned upstream of lacZ and their strength were compared by measuring the β-galactosidase activity of the cells transformed with promoter-reporter construct.

FIG. 6. Binding of *M. smegmatis* RNA polymerase to pSAK12 as seen by Gel mobility shift assay. 1) Lane Free DNA (pSAK12) 2) Lane 1:20 (pSAK12:RNA Polymerase) 3) Lane 1:30 (pSAK12: RNA Polymerase) 4) Lane 1:50 (pSAK12:RNA Polymerase) 5) Lane Free DNA (PGEM7Z) 6) Lane 1:20 (PGEM7Z:RNA polymerase) 7) Lane 1:30 (PGEM7Z:RNA polymerase) 8) Lane 1:50 (PGEM7Z:RNA polymerase).

FIG. 7. 8% denaturing PAGE of in vitro transcripts from pSAK12. Lane 1. Molecular weight marker, Lane 2. PGEM7z (single round transcription) Lane 3. pSAK12 (single round transcription)) Lane 4. pSAK12 (multiple round transcription) Lane 5. pSAK12+50 μg rifampicin (single round transcription).

FIG. 8. Mutagenesis of Three conserved T bases in putative −10 rel promoter region.

FIG. 9. Effect of three mutations on lacZ expression in *M. smegmatis*. a) pSD5B b) pAN12 c) pSS12 d) pSS22 e) pSS32.

SUMMARY OF THE INVENTION

Accordingly, the present invention relates to a promoter high-throughput screening for inhibitors against Mycobacteria under low carbon or starved conditions. Further, the use of this novel 200 bp promoter opens new vistas and provides a new system that would enable the TB drug developers to isolate and develop highly efficient inhibitors or medicines against ever evolving and changing *M. tuberculosis* mycobacteria.

DETAIL DESCRIPTION OF INVENTION

It has been observed that Mycobacteria have the characteristic of recurring in patients who have been inflicted by an attack of TB once. Many times the mycobacteria are also not completely eliminated by the medication. Further, mycobacteria reproduce themselves very fast and thus they cannot be eliminated by presently available strong drugs and multidrug therapy. Therefore, there is an imperative need to identify and develop new drugs. However, the presently available systems are inadequate to address this problem.

Previously there were no suitable models for drug screening against *Mycobacterium tuberculosis* (*M. tb*), which shows long term persistence within a host or known as latent *M. tb*. However, they are the major source of concern as actively growing or dividing species can be efficiently treated with major antibiotics.

The extremely slow growth rate of *M. tb* under latent conditions makes it a very unfriendly candidate for high throughput screening. Clearly, a model for latency is warranted which should show comparatively fast growth rate, and which can be manipulated with ease.

In the present invention mycobacteria, *M. smegmatis* which is fast growing and non-pathogenic, but a very close counter-part of *M. tuberculosis* has been used as a model system for identifying a novel promoter which allows the mycobacteria to survive under low carbon or starved conditions and to be resistant to multidrug therapy during treatment. The identified novel promoter has been identified to serve as a better system in developing new and efficient inhibitors against the mycobacteria. This novel isolated promoter is better and more efficient than the known promoters being used for identifying new and efficient inhibitors or drugs.

In the present invention the it has been shown that the 200 bp upstream fragment obtained from 1.5 kb rel promoter of *M. tuberculosis* is sufficient for promoter activity and is constitutive in nature. The promoter is stronger in comparison to hsp60 promoter. Such a simple blue/white selection and promoter specificity for mycobacterial RNA polymerase, would go a long way for both quantitative and qualitative assessment of the mycobacterial promoter strength. In addition, any gene cloned downstream of rel promoter in correct orientation would show good expression, expectedly. The stability of the plasmid for a considerable length of time is an added advantage. Although a regulatory, starvation controlled promoter element from a upstream sequence of the rel gene was unexpected, even the 1.5 kb upstream promoter sequence showed constitutive expression with xylE gene (FIG. 1) and thus we did not pursue this point further. There could be other regulatory elements which cannot be detected by the assay presented here. This system would find a wide range of application. The single round heparin-resistant transcription by *M. smegmatis* RNA polymerase reported here has not been reported in the literature earlier. Therefore in the present invention the reconstituted transcription machinery would help to dissect the mechanism of transcription regulation in mycobacteria and also show that the promoter is responsible for such functions, i.e., this specific promoter is activated only under the stress conditions which further activates the RNA polymerase activity thereby allowing the mycobacteria to survive under low carbon or starved conditions. Reconstitution of RNA polymerase from individual subunits will be an added advantage. Further, the use of this novel 200 bp promoter opens new vistas and provides a new system that would enable the TB drug developers to isolate and develop highly efficient inhibitors or medicines against ever evolving and changing *M. tuberculosis* mycobacteria.

In order to delineate the control of gene expression in Mycobacteria, one has to have an efficient reconstituted expression system and reconstituted RNA polymerase, the enzyme responsible of gene expression. U.S. Pat. No. 6,355,464 discusses the second goal. i.e., reconstitution of RNA polymerase from *M. tuberculosis* and describes high throughput screening of natural inhibitors against this reconstituted enzyme. However, their method fails to use an easy, high stringent assay of RNA polymerase or gene expression for this screening purpose. On the other hand, a detectable gene expression system can pinpoint the effect of inhibitors on a RNA polymerase based assay by looking at the level of expression. Moreover, a battery of inhibitors can be studied by varying the degree of response at different genes. The present study of a simple lacZ expression system used with rel promoters showed that this promoter is very efficient and thus can be engineered with any unknown open reading frame and then can be studied for their expressibility by transcribing them with mycobacterial RNA polymerase.

Accordingly, the main embodiment of the present invention relates to a promoter having a SEQ ID NO: 2 for high throughput screening and developing inhibitors of mycobacteria under low carbon source or starved conditions.

Yet another embodiment of the present invention relates to the a promoter wherein the promoter is 2.5 fold more active than the conventional $P_{hsp60}$ (heat shock protein expression system).

Another embodiment of the present invention relates to an expression system for high-throughput screening and developing inhibitors of mycobacteria under low carbon source or starved conditions wherein the system comprises a promoter of 200 bp having SEQ ID No:2 in a vector pSAK12.

One more embodiment of the present invention relates to a method of preparing a promoter expression system for high-throughput screening and developing inhibitors of mycobacteria under low carbon source, wherein the process comprises the steps of:

(a) isolating and characterizing a 200 bp promoter sequence having SEQ ID NO: 2 from nucleotide sequence of relA/spoT of *M. smegmatis* having a SEQ ID NO: 1, (b) ligating the isolated promoter sequence of step (a) in vector pSAK12, and (c) studying the expression of the promoter sequence under low carbon source or carbon starved conditions.

Still in another embodiment of the present invention, the carbon source, glucose, is in the range of about 2.5-0.001%.

In one more embodiment of the present invention, the carbon source, glucose, is in the range of about 2 to 0.02%.

Another embodiment of the present invention relates to a percentage of inhibition of growth of bacteria in the presence of the promoter and the inhibitor ethambutol being reduced in the range by about 6 to 25% in the presence of 0.02% glucose i.e., under starved conditions.

Still another embodiment of the present invention relates to a percentage of inhibition of growth of bacteria in presence of the promoter and in the presence of the inhibitor ethambutol being reduced in the range by about 7 to 21% in the presence of 0.02% glucose i.e., under starved conditions.

One more embodiment of the present invention relates to a percentage of inhibition of growth of bacteria in the presence of the promoter and the inhibitor isoniazid being reduced in the range by about 15 to 45% in the presence of 0.02% glucose i.e., under starved conditions.

Another embodiment of the present invention relates to a percentage of inhibition of growth of bacteria in the presence of the promoter and the inhibitor isoniazid is reduced in the range by about 18 to 40% in the presence of 0.02% glucose i.e., under starved conditions.

Still another embodiment of the present invention relates to the wherein percentage inhibition growth of bacteria in the presence of the promoter and the inhibitor rifampicin is reduced in the range by about 20 to 45% in the presence of 0.02% glucose i.e., under starved conditions.

Yet another embodiment of the present invention relates to the percentage inhibition growth of bacteria in the presence of the promoter and the inhibitor rifampicin is reduced in the range by about 21 to 41% in presence of 0.02% glucose, i.e., under starved conditions.

The following examples are given by way of illustration of the present invention and therefore should not be construed to limit the scope of the present invention.

EXAMPLES

Example 1

Bacterial Strains, Medium and Growth Condition

All the plasmids used in this study are enlisted in Table 1. *Mycobacterium smegmatis*, mc$^2$155, was used in all the experiments. The bacteria were grown in 7H9 medium supplemented with 2% glucose, 0.05% Tween-80 and 25 µg/ml kanamycin, unless mentioned otherwise. For plate culture, 1.5% agar was added to the liquid medium. For plate assay of lacZ, bacteria were grown in 7H9 plate containing 40 µg/ml of X-gal. The *E. coli* strains were maintained in LB or LB agar with either 50 µg/ml of kanamycin or 100 µg/ml of ampicillin.

Example 2

Transcriptional Fusion of *M. tuberculosis* RelA/SpoT to XylE Reporter

The BamHI-SphI fragment which contained 1.5 kb upstream to start codon of *M. tuberculosis* relA/spoT was taken out from the cosmid MTCY227 (a gift from S. T. Cole: Cole et. al. 1998) and subcloned in the BamHI-SphI site of pTZ19U (Bio-Rad). Then the fragment was released by KpnI-BglII site and cloned into KpnI-BamHI site of pTKmx (Kenney and Churchward, 1996). The resulting recombinant plasmid, pAKO1, had the xylE reporter transcriptionally fused to the 221$^{st}$ nucleotide of relA/spoT gene (Table 1).

Example 3

Measurement of Transcriptional Activity of the Sequence Upstream to RelA/SpoT The *M. smegmatis*, mc$^2$155, transformed with pAKO1 was cultured till the mid-log phase (OD$_{600}$=0.7) in 7H9 medium (with 2% glucose, 0.05% Tween-80 and 25 µg/ml kanamycin) and then harvested, washed and transferred to 7H9 medium containing either 2% glucose, 0.2% glucose, or, 0.02% glucose and assayed for xylenase activity at different time intervals. The xylenase assay was carried out as described previously (Kenney and Churchward, 1996). Briefly, cells from 1 ml culture were harvested, resuspended in 50 µl of PBS and then 10 µl of cell suspension was added to 990 µl of 0.5 mM of Catechol. The reaction mix was incubated at room temperature for 10 minutes and then OD$_{375}$ was obtained. The OD contributed by scattering of cells was also measured at 375 nm. The activity/unit OD was calculated from the formula (Dastur and Varshney, 2001).

$$\text{Activity/unit } OD = \frac{[OD_{375}(\text{reaction mix}) - OD_{375}(\text{cell density})]}{[OD_{375}(\text{cell density})]}$$

Cells transformed with pTKmx were used as a negative control for the assay. The activities obtained for pTKmx was subtracted from the activities obtained for pAKO1 (Table 1).

Example 4

Cloning and Characterization of 200 bp Upstream Sequence Proximal to the Start Codon of RelA/SpoT A set of two primers sak1 (CGGCCACGTTCGGTAC-CTCCGACCTAGA) (SEQ ID NO:3) and sak2 (GCCGT-GTCGTGAGAATTCACGACGTGTTAG) (SEQ ID NO:4) were used to amplify the 200 bp immediately upstream to relA/spoT (see FIG. 1) from pAKO1. The PCR conditions were 94° C. for 1 min., 66° C. for 30 sec and 72° C. for 30 sec. The 200 bp amplicon was subcloned into pGEM-T Easy (Promega) to form pSAK12. The vector pGEM-T Easy is a linear vector with a single T overhang on either arm, which is flanked by multiple cloning sites. The linear vector with T overhang ligates to any PCR product which has A at the terminals (invariably added as a last base when Taq DNA polymerase is used in PCR). The clone with the correct orientation (the end proximal to the gene was towards SphI site) was picked and the 200 bp insert was released by SphI-SpeI and ligated to SphI-XbaI ends of pSD5B (Jain et. al. 1997) to form a recombinant plasmid pAN12. pSD5B is a mycobacteria-*E. coli* shuttle vector with a promoterless lacZ. The promoter activity of the 200 bp fragment was analyzed by assaying the lacZ activity of the *M. smegmatis* transformed with pAN12. The lacZ activity was assayed on plate as well as liquid culture as published earlier (Miller, 1972). *M. smegmatis* transformed with pSD5B was used as a negative control.

For a comparative analysis between the promoter strength of 200 bp fragment and the P$_{hsp60}$, the fragment containing lacZ was released from pSD5B by PstI digestion and ligated to pMV261 (Stover et al., 1991) at PstI site and screened for the correct orientation. The recombinant plasmid in correct orientation, pHsplac, in which lacZ was cloned in the direction of the Phsp60 was screened for further use. The lacZ activity of *M. smegmatis* cells transformed with pHsplac was compared with that of the cells harboring pAN12 in plate as well in liquid culture. The stability of pAN12 in the host strain, both *M. smegmatis* and *E. coli* was further checked by repeated subculturing for 10 generations, expressing lacZ gene on X-gal containing plate. Restriction analysis revealed that there is no addition or deletion of the sequence in the plasmid (Table 1).

TABLE 1

Catalogue of all the plasmids used

| Plasmid | Size(bp) | Marker | Description |
|---|---|---|---|
| pTKmx | 5998 | Kan$^R$ | pTKmx is a shuttle vector containing promoterless xylE gene |
| PAKO1 | 6208 | Kan$^R$ | pTKmx with 1.5 kb DNA fragment, upstream to start codon of *M. tuberculosis* relA/spoT, cloned upstream of xylE gene |
| PGEMT Easy | 3010 | Amp$^R$ | PGEMT Easy vector (supplied from promega) |
| PGEM7Z | 2998 | Amp$^R$ | Same as PGEMT Easy vector (supplied from promega) |
| pSAK12 | 3231 | Amp$^R$ | PGEMT Easy vector with 200 bp DNA fragment, upstream to start codon of *M. tuberculosis* relA/spoT, cloned upstream of lacZ gene |
| pSD5B | 9500 | Kan$^R$ | pSD5B is ashuttle vector containing promoterless lacZ gene |
| pAN12 | 9760 | Kan$^R$ | pSD5B with 200 bp DNA fragment, upstream to start codon of *M. tuberculosis* relA/spoT, cloned upstream of lacZ gene |
| pSS12 | 9760 | Kan$^R$ | 1$^{st}$ 'T' of −10 region of promoter mutated to 'G' in pAN12 |
| pSS22 | 9760 | Kan$^R$ | 2$^{nd}$ 'T' of −10 region of promoter mutated to 'G' in pAN12 |
| PSS32 | 9760 | Kan$^R$ | 3$^{rd}$ 'T' of −10 region of promoter mutated to 'G' in pAN12 |

Example 5

Gel Retardation and Single Round Transcription with *M. smegmatis* RNA Polymerase RNA polymerase from mid-log phase cells of mc$^2$155, *M. smegmatis* was purified according to the known protocol (Burgess and Jendrisak, 1975) mainly following the established method for purification of the *E. coli* enzyme. The purified enzyme shows full complementation of all the subunits ($\alpha^2\beta\beta^1\omega$) and two sigma subunits ($\sigma^A$ and $\sigma^B$) (not shown).

0.1 pmole of DNA template pSAK12 was incubated with 20, 30 and 50 fold molar excess of *M. smegmatis* RNA polymerase in the presence of a buffer containing 50 mM Potassium glutamate, 250 mM Tris-HCl (pH 7.8), 15 mM Magnesium acetate, 0.5 mM Dithiothreitol, 0.5 mM EDTA, 250

µg/ml Bovine serum albumin and 25% glycerol. The incubation was carried out for 30 minutes at 37° C. The bound and unbound form of DNA was resolved on a 0.7% Agarose gel against 1×TBE buffer.

Example 6

In Vitro Transcription Assay 0.2 pmole of linearized form of pSAK12 and 2 pmole of *M. smegmatis* RNA polymerase were mixed in transcriptional buffer containing 500 mM Tris-HCl (pH 7.8), 30 mM Magnesium acetate, 1 mM EDTA, 1 mM DTT, 500 mM NaCl 300 µg/ml BSA in a final volume of 35 µl and incubated at 37° C. for 45 minutes. The reactions were started by adding 15 µl of prewarmed substrate-heparin mixture which contained 1.5 µl of 10× transcriptional buffer, 2 µl of 25×NTP mixture (4 mM each of ATP, CTP, GTP, 1.25 mM UTP and 2 µCi of $\beta^{32}$p UTP (3000 cimmol$^{-1}$) and 2 µl of 5 mg/ml of heparin (sodium salt). The reaction was allowed to proceed for 15 minutes at 37° C. and stopped by addition of 50 µl of a stop solution containing 40 mM EDTA and 300 µg/ml yeast tRNA. Transcriptional product was precipitated overnight at −20° C. by adding $\frac{1}{10}^{th}$ volume of 3M sodium acetate (pH 5.2) and 2.5 volume of 100% ethanol. The precipitate was washed with 70% ethanol and dried, dissolved in 15 µl of deionized formamide loading dye, heated to 90° C. for 5 minutes and cooled on ice. The precipitate was loaded on a 8% denaturing polyacrylamide gel containing 7M urea and run in 1×TBE at constant 250 volt. The gel was dried and exposed to X-ray films for 24 hours at −70° C. For multiple round transcription, the reaction was carried out in the same way as the single round transcription excluding the addition of heparin. In order to study the inhibition of single round transcription, the reaction was carried out in the presence of 50 µg of rifampicin (Table 2). This in vitro study highlights the gist and aim of the experiment, wherein the inventors have used stationary phase or starvation induced promoter in expression vector pSAK12. The novel promoter like this can be assayed for inhibition of transcription activity and thus indirectly reflects the growth of the organism in the presence of antibiotics or inhibitors. This assay demonstrates that due to the activation of this promoter under starved or low carbon source conditions there is higher transcription thereby enhancing the percentage of survival of mycobacteria. In other words, in the presence of classical inhibitors, for example rifampicin, normal promoters inhibit only 50 to 70 percent inhibition of growth, whereas the same inhibition is reduced by about 20% in the presence of the promoter of the present invention under a stationary or a starved state.

TABLE 2

| Drug | Concentration (µgm/ml) | % inhibition of growth at* 2% Glucose | 0.02% Glucose |
|---|---|---|---|
| Ethambutol | 0.15 | 44 | 37 |
|  | 0.31 | 85 | 66 |
|  | 0.63 | 91 | 68 |
|  | 1.25 | 93 | 72 |
| Isoniazide | 0.8 | 33 | 12 |
|  | 1.6 | 70 | 30 |
|  | 3.2 | 90 | 70 |
|  | 6.4 | 96 | 78 |
| Rifampicin | 0.25 | 39 | 9 |
|  | 0.5 | 58 | 17 |
|  | 1.0 | 70 | 29 |
|  | 2.0 | 89 | 68 |

*Percent inhibition growth at each point is the relative decrease in the optical density of liquid culture as compared to the control (without antibiotic).

Example 7

Mutation of the Promoter Element

Site-specific mutagenesis was carried out by the quick-change protocol (Stratagene) in the −10 region of the promoter (TATCCT). The three highly conserved T bases in the −10 region of the promoter were mutated to either G or C bases. The PCR conditions were 94° C. for 3 min, 65° C. for 30 sec and 72° C. for 3 min, using pSAK12 as template. The mutations were confirmed by sequencing of the DNA. 200 bp inserts both wild type and mutants were released by SphI-SpeI of pSAK12 and ligated to SphI-XbaI ends of pSD5B (Jain et al. 1997) to form pSS12, pSS22, pSS32. The strategy of molecular cloning was followed according to Sambrook et. al., 1989. The electroporation of *M. smegmatis* was carried out in cell electroporator (BTX) with 2 mm-gap cuvette at 1.25 kV/mm.

Example 8

The 1.5 kb DNA fragment upstream of relA/spoT ORF has a constitutive promoter activity.

The 1.5 kb DNA fragment upstream of relA/spoT showed promoter activity when cloned in xylE reporter system (Kenney and Churchward, 1996) on pAKO1 (FIG. 2). Surprisingly, the activity was constitutive with negligible change when shifted to a carbon starved medium. Moreover, there was a very strong level of expression even in a carbon enriched culture. As a 1.5 kb fragment was too big for promoter analysis, a search for promoter element nearest to relA/spoT was carried out using nested PCR.

Example 9

The promoter activity of the large fragment was contained in a 200 bp sequence immediately upstream to relA/spoT.

Figure 3A:
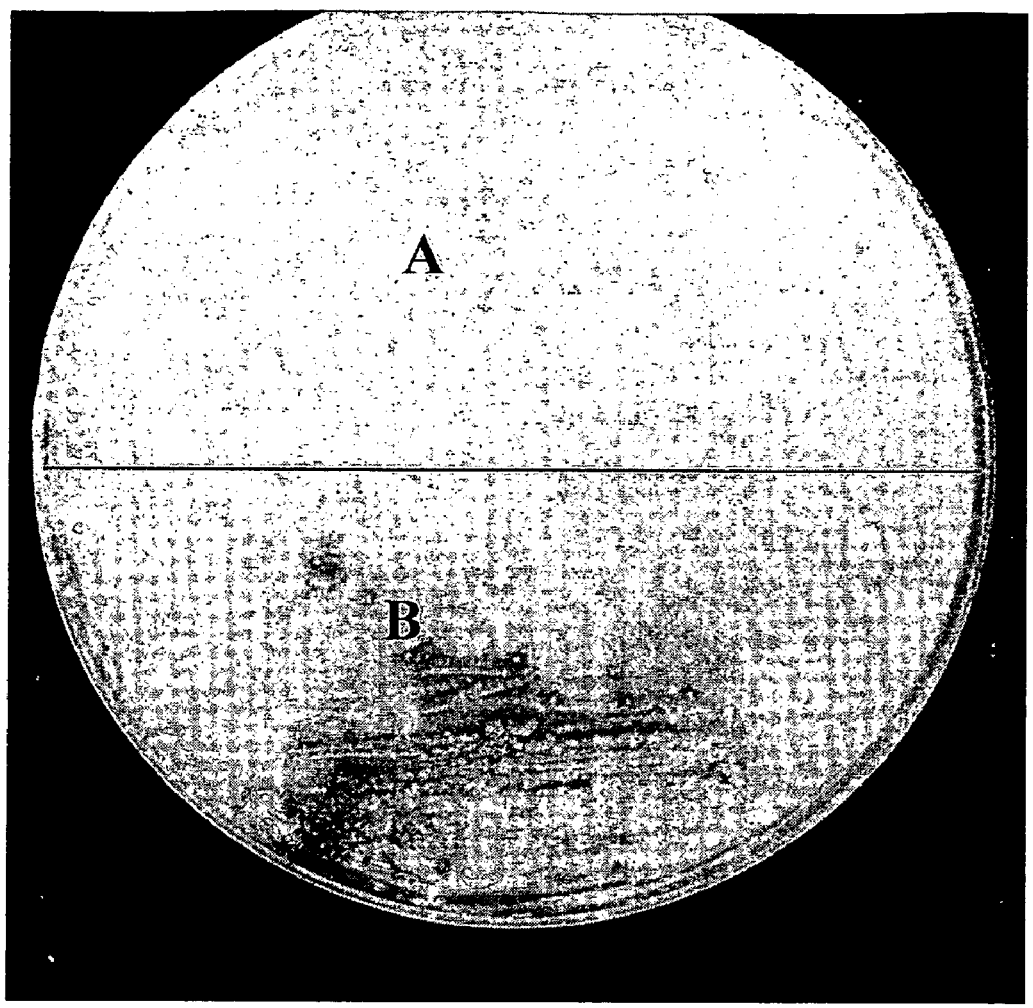
Figure 3B:
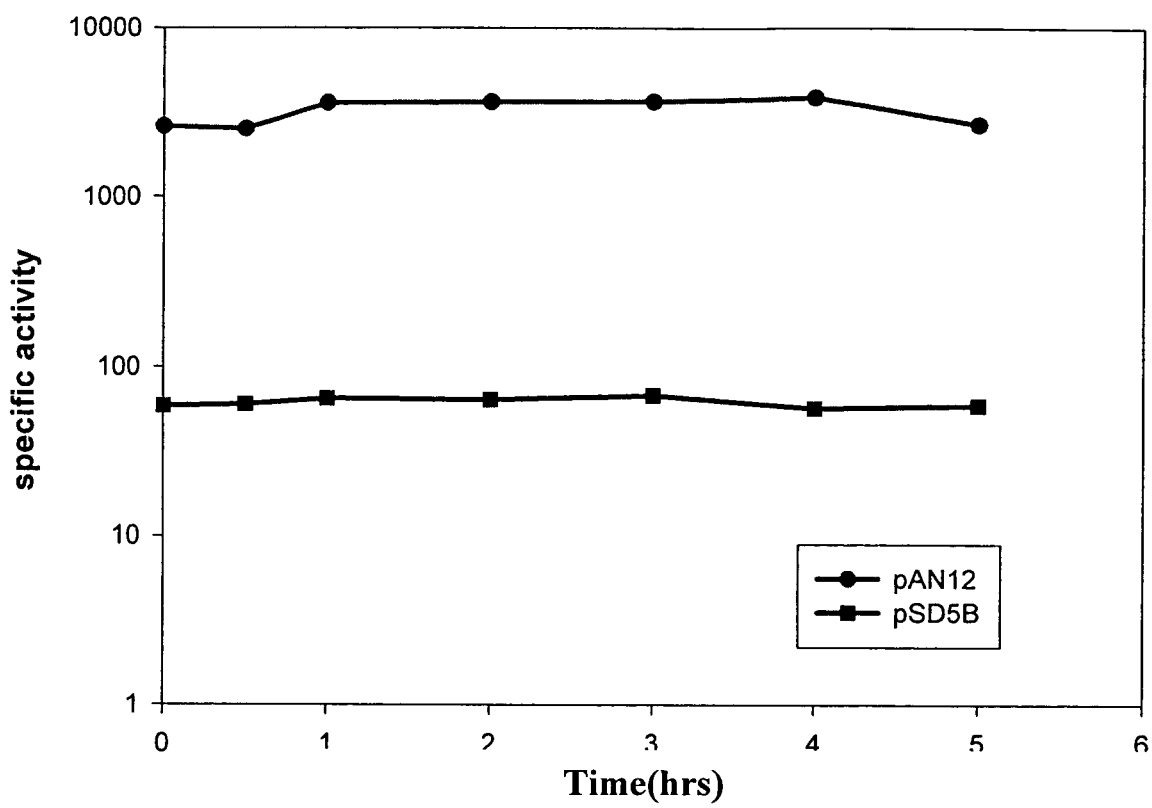

With a set of two primers, sak1 and sak2, a 200 bp DNA fragment upstream to relA/spoT was amplified and cloned ahead of lacZ reporter system (Jain et al., 1997) to form promoter-reporter construct on pAN12. FIG. 3a shows that 200 bp fragment was sufficient to produce the promoter activity which appears to be similar in strength to that of entire 1.5 kb. A quantitative analysis of the promoter-lacZ system in liquid culture (FIG. 3b) corroborated the data obtained with plate culture. Consistent with the promoter activity of 1.5 kb with xylE reporter, the activity of 200 bp was observed to be constitutive with a high level of expression even under nutrient enriched conditions at a zero time point. In carbon starved condition, not additional increase in β-galactosidase activity was noticed. Although a set of nested PCR products with increments of 200 bp were also amplified, they were not analyzed further since the entire promoter activity was observed in the proximal 200 bp fragment. For further work we have referred to this fragment as $P_{relMt}$.

Figure 4:
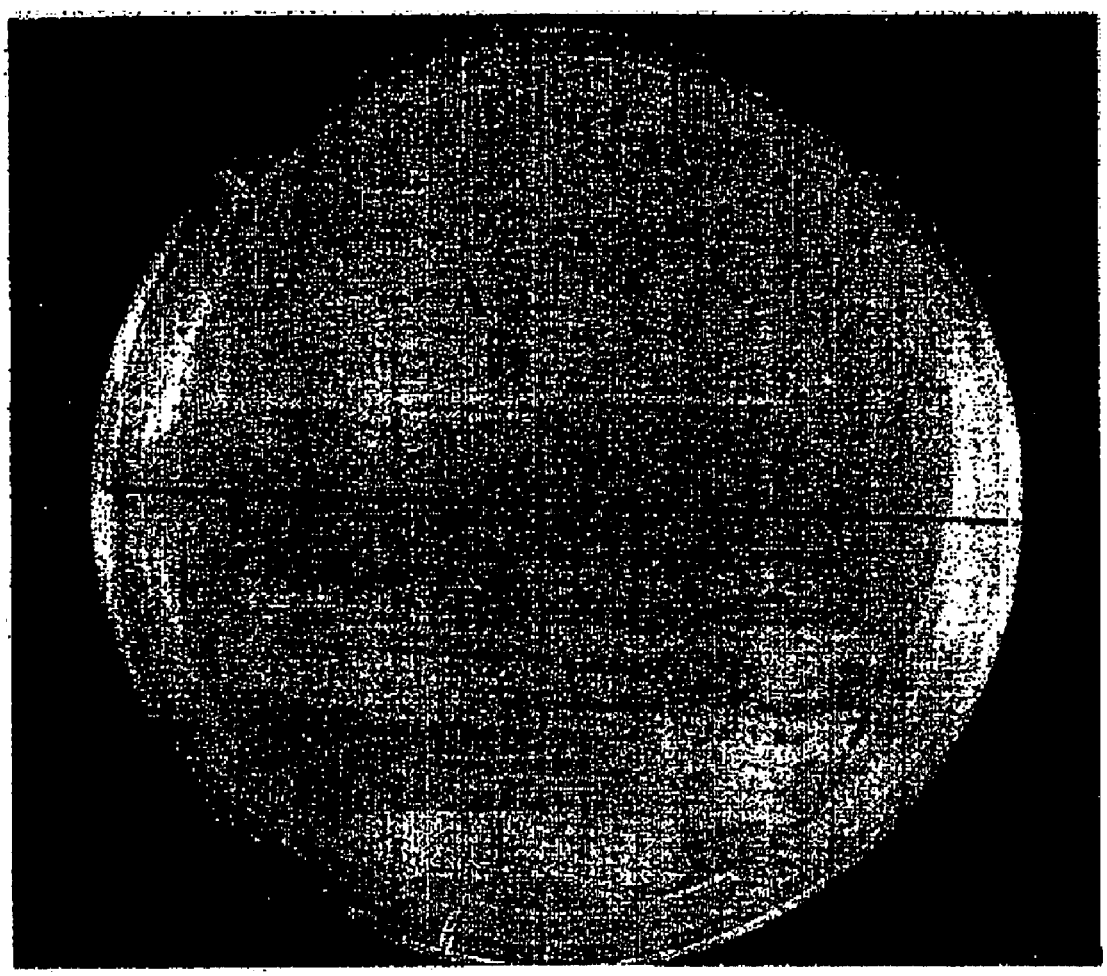

Interestingly, the promoter activity of the 200 bp fragment was specific to mycobacteria and was completely lost in *E. coli* (FIG. 4). This observation was consistent with the general property of most of the *M. tuberculosis* promoters that they are not active in *E. coli* (Dasgupta et. al., 1993; for review see Mulder et. al., 1997).

Example 10

Figure 5A:
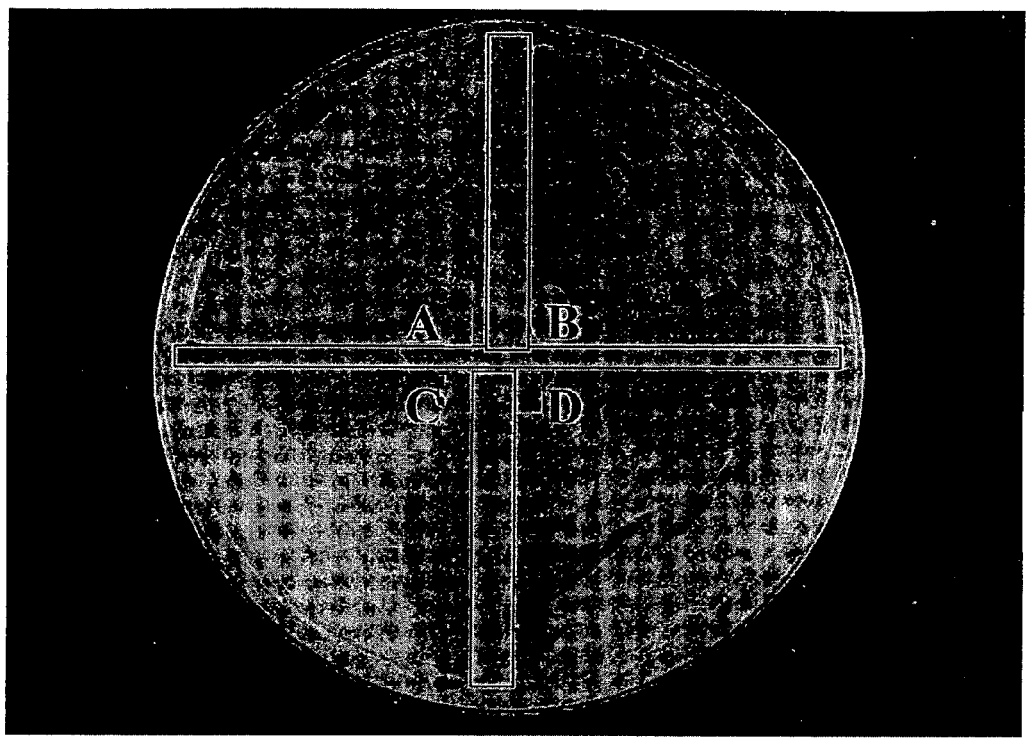

Promoter Activity of $P_{relMt}$ was Stronger than $P_{hsp60}$ and Promoter Directed Transcription As the promoter was constitutive and had a high basal level of expression, we compared the activity of this promoter with a widely used mycobacterial hsp60 promoter (FIG. 5a). $P_{hsp60}$ is one of the most common mycobacterial promoters used for in vivo gene expression (Stover et al., 1991) and in vitro transcription (Levin and Hatfull, 1993). The strength of the promoter was measured as a direct function of activity produced by the promoter fragment. For comparative analysis, lacZ was cloned downstream to $P_{hsp60}$ in pMV261 (Stover et. al., 1991). As the two promoter-reporter constructs were different, the final lacZ activities from the two constructs, $P_{hsp60}$-lacZ and $P_{relMt}$-lacZ, were obtained as the percentage increase in the activity due to the presence of the promoter. It was calculated as:

$$\text{Percentage increase in specific activity} = \frac{sp.act.\ (lacZ + \text{promoter}) - sp.act.\ (\text{empty vector})}{sp.act\ (\text{empty vector})}$$

Figure 5B:
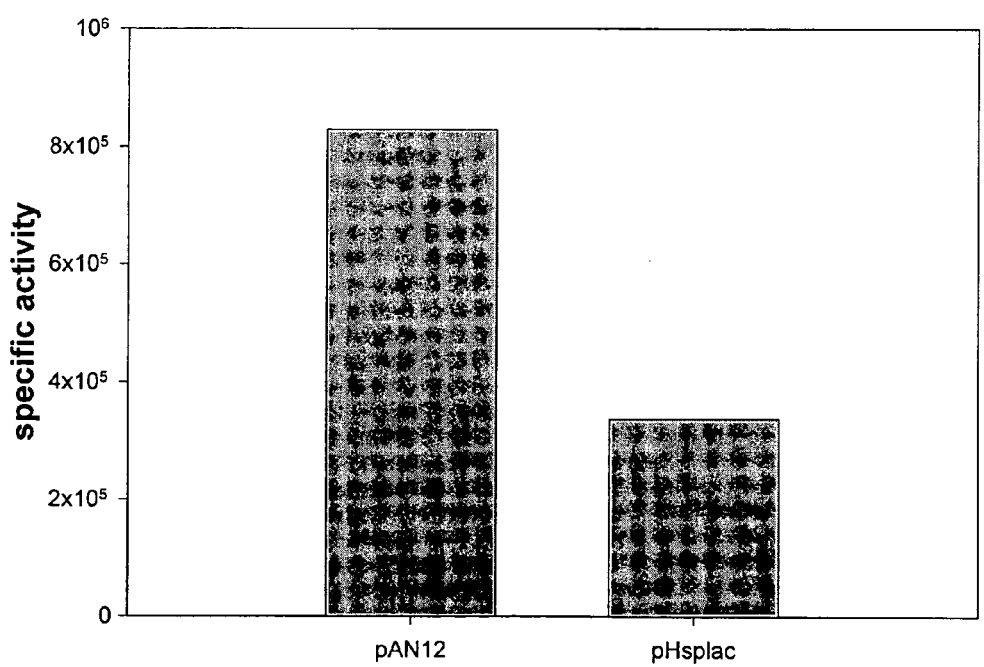

FIG. 5 a & b show that $P_{hsp60}$ was at least 2.5 fold less active as compared to $P_{relMt}$. This observation suggested that $P_{relMt}$ might be a better template for developing a mycobacterial in vitro transcription system. Thus, we explored whether $P_{relMt}$ can be used as a template for in vitro transcription.

Example 11

M. smegmatis RNA Polymerase Binds to pSAK12 Promoter Directed Transcription

Figure 6:
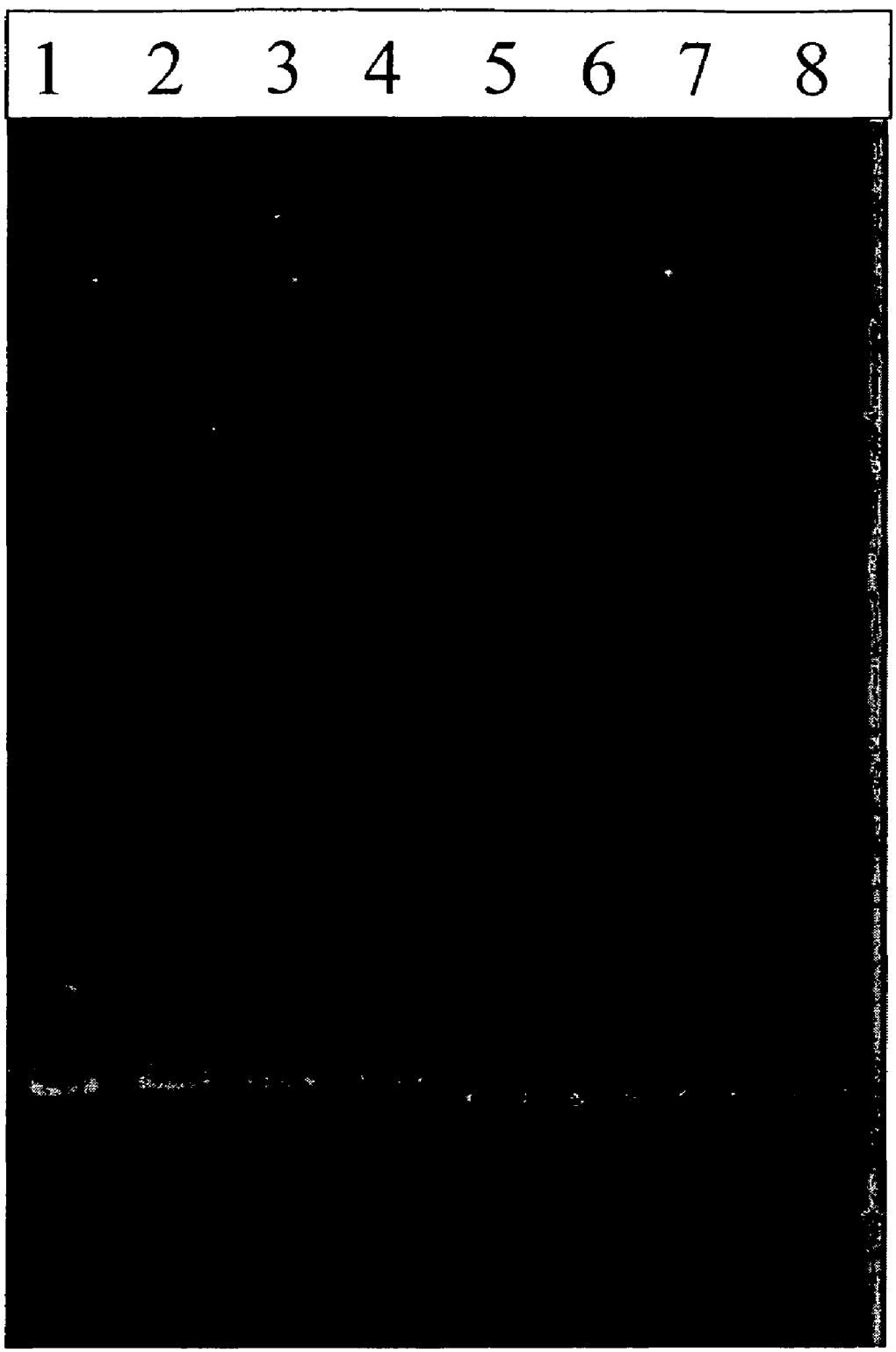

FIG. 6 shows the electrophoretic mobility shift assay of pSAK12 with M. smegmatis RNA polymerase at a varying molar ratio. It can be seen from the figure that the vector without a 200 base pair rel promoter sequence, cannot bind the enzyme at any concentration (lanes 6-8) where as pSAK12 shows appreciable protein concentration dependent mobility shift with RNA polymerase (lanes 2-4).

Figure 7:
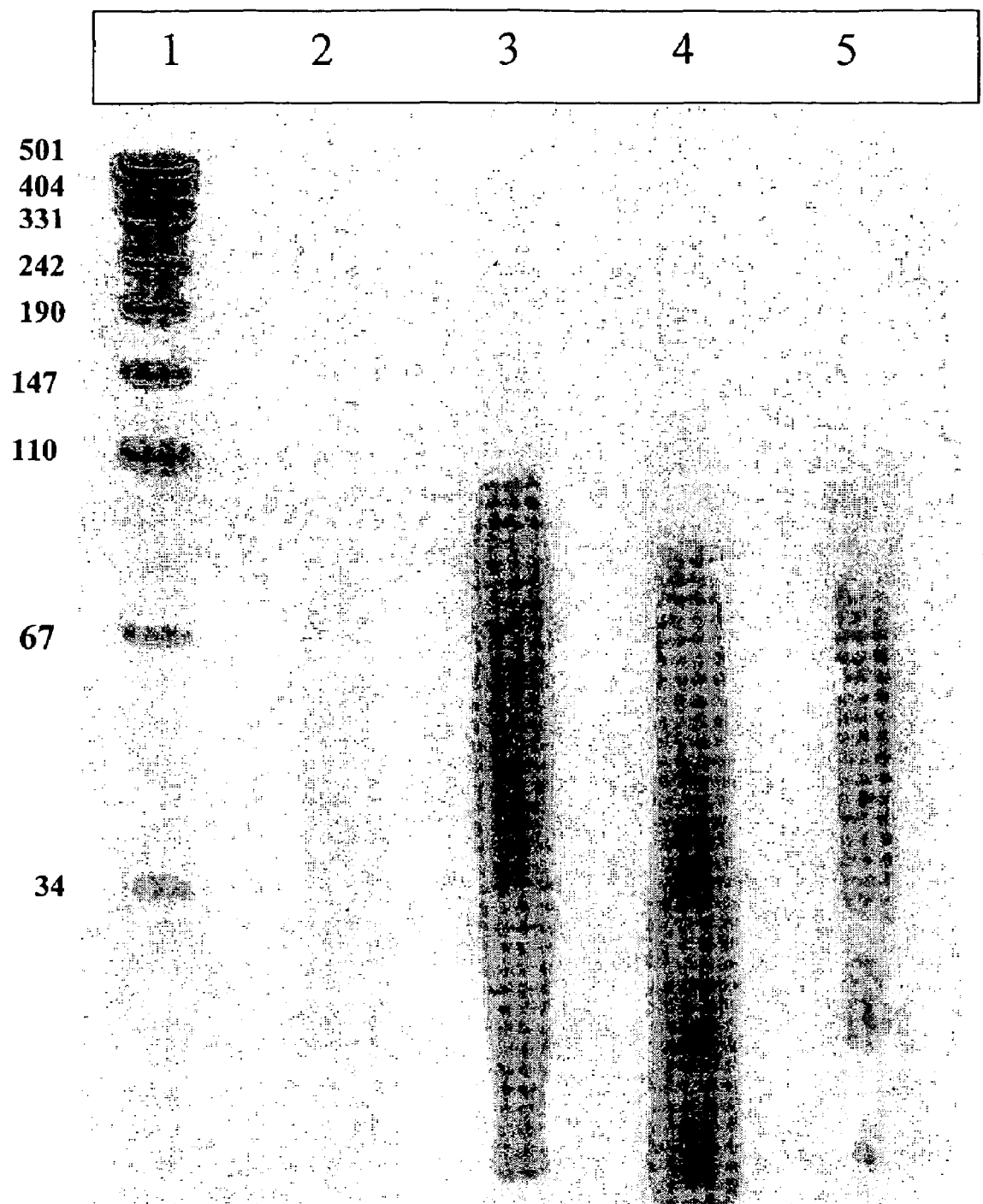

It was observed a very specific influence of 200 bp upstream region of rel promoter in RNA polymerase recognition from previous experiment, it was thought that the promoter specific transcription reaction can also be detected (FIG. 7). It can be seen from lanes 3 and 4 that a short transcript was generated (≈37 bp) both in single and multiple round transcription which was rifampicin sensitive (lane 5).

Example 12

Detection of Promoter Element

Figure 9:

Putative mycobacterial sequences, published by Mulder et al., (1997), showed the M. tuberculosis promoter consists of a −10 consensus sequence TAyGAT(y-pyrimidine). Putative −10 consensus TATCCT sequence were identified in the 200 bp promoter region of rel. The putative −10 consensus sequence of rel promoter are highly conserved at four positions as that of −10 consensus sequence. FIG. 8 shows varying degree of conserved T base in the −10 promoter sequence. Thus the $1^{st}$ position T base was mutated to G position, $3^{rd}$ position T was mutated to G position, $6^{th}$ position T was mutated to C position and their effect on lacZ expression was studied. FIG. 9 shows that the third T base which is 100% conserved had the maximum effect on lacZ expression as expected.

Advantage Over Existing Methods:

In order to delineate the control of gene expression in Mycobacteria, one has to have an efficient reconstituted expression system and reconstituted RNA polymerase, the enzyme responsible of gene expression. An US patent (U.S. Pat. No. 6,355,464 B1, dated Mar. 12, 2002) has already been granted towards the second goal i.e., reconstitution of RNA polymerase from M. tuberculosis. They have reported the high throughput screening of natural inhibitors against this reconstituted enzyme. However, their method fails to use an easy, high stringent assay of RNA polymerase or gene expression for this screening purpose. On the other hand, a detectable gene expression system can pinpoint the effect of inhibitors on RNA polymerase based assay by looking at the level of expression. Moreover, a battery of inhibitors can be studied by varying degree of response at different genes. Our simple lacZ expression system used with rel promoters showed that this promoter is very efficient and thus can be engineered with any unknown open reading frame and then can be studied for their expressibility by transcribing them with mycobacterial RNA polymerase.

The two well known expression system used world-wide for mycobacteria are BCG heat shock induced promoter hsp60 and the other is acetamide inducible system. It is shown that at least in one case (hsp60) the promoter (rel) of the present invention is much better and difference between them has been estimated in quantitative terms.

We claim:

1. An isolated polynucleotide fragment from *Mycobacterium* consisting of SEQ ID NO: 2 which contains a promoter.

2. The *Mycobacterium* promoter of claim 1, wherein the promoter is operatively linked to a reporter gene LacZ.

3. The *Mycobacterium* promoter of claim 1, wherein the promoter is operatively linked to a reporter gene xylE.

4. The *Mycobacterium* promoter of claim 1, wherein the promoter is 2.5 fold more active in *M. smegmatis* than a heat shock protein 60 promoter, $P_{hsp60}$.

5. The *Mycobacterium* promoter of claim 1, wherein the promoter is further contained in a plasmid with an Ampicillin or Kanamycin resistance marker.

* * * * *